United States Patent
Wulf et al.

(10) Patent No.: US 9,820,687 B2
(45) Date of Patent: Nov. 21, 2017

(54) METHOD FOR DETERMINING DROWSINESS

(71) Applicant: Robert Bosch GmbH, Stuttgart (DE)

(72) Inventors: Felix Wulf, Ludwigsburg (DE); Tjark Vandommele, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 15/374,795

(22) Filed: Dec. 9, 2016

(65) Prior Publication Data

US 2017/0164883 A1 Jun. 15, 2017

(30) Foreign Application Priority Data

Dec. 10, 2015 (DE) ........................ 10 2015 224 889

(51) Int. Cl.
*G08B 23/00* (2006.01)
*A61B 5/18* (2006.01)
*B60Q 5/00* (2006.01)
*B60Q 9/00* (2006.01)
*A61B 5/11* (2006.01)

(52) U.S. Cl.
CPC ............ *A61B 5/18* (2013.01); *A61B 5/1128* (2013.01); *B60Q 5/005* (2013.01); *B60Q 9/00* (2013.01); *A61B 5/1103* (2013.01)

(58) Field of Classification Search
CPC ....... A61B 5/18; A61B 5/1128; A61B 5/1103; A61B 5/6893; A61B 5/0077; B60R 11/04; B60Q 5/005; B60Q 9/00
USPC ........................................................ 340/576
See application file for complete search history.

(56) References Cited

U.S. PATENT DOCUMENTS

| | | | |
|---|---|---|---|
| 7,663,495 B2 | 2/2010 | Haque et al. | |
| 8,009,051 B2 | 8/2011 | Omi | |
| 9,198,575 B1* | 12/2015 | Blacutt | G06K 9/00845 |
| 2008/0204256 A1* | 8/2008 | Omi | G08B 21/06 340/575 |
| 2012/0089553 A1* | 4/2012 | Mollicone | G06F 19/3431 706/52 |
| 2016/0167671 A1 | 6/2016 | Offenhaeuser et al. | |

FOREIGN PATENT DOCUMENTS

| | | |
|---|---|---|
| DE | 10126224 A1 | 12/2002 |
| DE | 102011122414 A1 | 6/2013 |
| DE | 102013213236 A1 | 1/2015 |
| DE | 102014210279 A1 | 12/2015 |

* cited by examiner

*Primary Examiner* — Dhaval Patel
(74) *Attorney, Agent, or Firm* — Norton Rose Fulbright US LLP; Gerard Messina

(57) ABSTRACT

A method for determining a drowsiness value that represents the drowsiness of a driver of a motor vehicle and is determined cyclically over defined time intervals on the basis of at least one drowsiness characteristic, includes the task of determining a drowsiness value of a time interval to be assessed, in addition to the drowsiness characteristic, at least one drowsiness base value is taken into account.

16 Claims, 2 Drawing Sheets

METHOD FOR DETERMINING DROWSINESS

RELATED APPLICATION INFORMATION

The present application claims priority to and the benefit of German patent application no. 10 2015 224 889.5, which was filed in Germany on Dec. 10, 2015, the disclosure of which is incorporated herein by reference.

FIELD OF THE INVENTION

The present invention relates to a method for determining a drowsiness value that represents the drowsiness of a driver of a motor vehicle and is determined cyclically over defined time intervals on the basis of at least one drowsiness characteristic.

BACKGROUND INFORMATION

For example, the Patent Application DE 10 2014 210 279 A1 is from the related art. This patent relates to a method for detecting the state of attention of the driver of a vehicle, in which the time characteristic of the vehicle speed is compared to a reference characteristic, and a signal corresponding to a reduced state of attention is generated if the time characteristic of the vehicle speed deviates by a defined amount from the reference characteristic. In this case, it is also mentioned that the gestures, facial expressions or the eye behavior of the driver is/are taken into account, a signal corresponding to a reduced state of attention being generated if the gestures, facial expressions or eye behavior point to behavior typical for drowsiness.

The document DE 10126224 A1 is from the related art. This document relates to a method and a device for its implementation, in order to characterize the state of the driver of a motor vehicle. A driver-state monitor determines variables concerning the physiological state of the driver. Depending on the ascertained result, control units of the motor vehicle are acted upon, as well as the driver, in order to implement measures suitable for maintaining a safe state of the driver and of the motor vehicle. As physiological state variables, in particular, brain waves are determined by electroencephalogram, the condition of the heart is determined by electrocardiogram, and blood pressure, heart rate or pulse, heart motion, skin temperature and conductance of the skin are determined and possibly stored. The eye-blinking rate, the force with which the driver grips the steering wheel and his movements on the seat may be determined as further key parameters, evaluated in relevant manner, and combined with the other results in order to initiate measures capable of influencing the vehicle and driver.

In existing systems for assessing sleepiness, in order to estimate the sleepiness (sleepiness and drowsiness are used as synonyms within the context of this patent application), attention is paid to specific features of individual blinking events like, for example, the amplitude or the speed of the lid movement. In so doing, in each case the values for blinking events within one specific period of time are utilized to assess the sleepiness. The input signals used for the regression of the sleepiness may represent blinking-related values like, e.g., the blinking amplitude or duration. However, other values calculated from the eyelid-opening signal are also used, such as the PERCLOS value—the eye opening averaged over a certain period of time of, e.g., 60 seconds.

In existing systems for assessing the sleepiness of a driver, the assessment is based solely on the instantaneously available features such as PERCLOS or blinking-related features, for example, calculated from an eyelid-opening signal. In some versions, the input values are also averaged over a certain period of time. However, it remains the case that an estimated sleepiness value is always determined from the input quantities of one specific period of time. As a result, the respective next estimated sleepiness value does not refer to the previous period of time.

In this context, it is not considered that as a rule, sleepiness does not develop suddenly. Nevertheless, in principle, there is the possibility that the output value of the sleepiness estimate could make big leaps, for example, on the basis of a specific situation measured at certain points in the case of the driver, or perhaps because of possible measuring inaccuracies or measuring errors.

SUMMARY OF THE INVENTION

The method of the present invention advantageously facilitates an increase in the quality of the results, especially an optimized evaluation with a high surety of ascertaining the actual state of drowsiness of the driver.

According to the present invention, this is rendered possible by the features set forth herein. Further embodiments of the invention are the subject matter the further descriptions herein and the additional descriptions herein.

The method according to the present invention for determining a drowsiness value that represents the drowsiness of a driver of a motor vehicle and is determined cyclically over defined time intervals on the basis of at least one drowsiness characteristic, is characterized in that in determining a drowsiness value of a time interval to be assessed, in addition to the drowsiness characteristic, at least one drowsiness base value is taken into account.

In this context, the term drowsiness value in particular includes a classification of drowsiness. Such a classification may include the evaluation of data as well as an estimate of a state of alertness and/or reflex capacity, etc., of the driver of a vehicle. The determination of the drowsiness value makes it possible to carry out suitable actions, e.g., a warning to the driver, in timely fashion.

A drowsiness value is determined on the basis of a so-called drowsiness characteristic. For this purpose, data from what is referred to as the eyelid-opening signal may be used in order to detect blinking events and to calculate specific parameters (drowsiness characteristic) for these blinking events. In addition, from the eyelid-opening signal, other features not related to blinking like, for example, PERCLOS are also extracted, which likewise may be used as drowsiness characteristic. Naturally, several drowsiness characteristics may be considered, as well. To determine the drowsiness value, first of all, the relevant drowsiness characteristics are defined and established. Subsequently, data is collected concerning the development of the drowsiness characteristic over a time interval. That is, for example, the values of the drowsiness characteristic over the individual time steps of the respective time interval. A time interval is understood to be a defined time span. For instance, it may amount to a few seconds, e.g., 30 seconds, up to several minutes, e.g., 20 min. Advantageously, such a time interval amounts to 3 minutes.

Naturally, the individual time steps for measuring the instantaneous development and magnitude of the drowsiness characteristic are correspondingly finer, that is, shorter. Often, they are contingent on the technical device used for the determination, for example, the picture frequency in the case of a camera. The collected data is subsequently evaluated. These steps are also executable by the use of various methods and/or various devices.

The ascertainment of the data with respect to the drowsiness characteristic over the time interval may advantageously be carried out as a continuous measurement over the time interval. The evaluation takes place over the defined time interval. To that end, the data may advantageously be preprocessed, e.g., with the aid of a moving average in order to smooth the values.

Various processes may be used advantageously to determine the drowsiness value from the drowsiness characteristics. For instance, classification processes or regression processes may be named, such as multiple linear regression, decision trees, artificial neural networks and various others. These processes are able to take different weightings of the input quantities into account. These may also sometimes be employed during the training of the process itself.

Through such a method, it is possible to increase the quality of the evaluation results. First of all, an isolated snapshot in time is avoided owing to the method. In addition, optimized accuracy of the actual results, as well as increased reliability in the evaluation and assessment of the instantaneous situation may thereby be attained.

In one advantageous specific embodiment, the method is characterized in that an ascertained drowsiness value of a prior time interval is taken into account as drowsiness base value.

As already explained, a drowsiness base value is considered in determining the drowsiness value of the time interval to be assessed. As such, for example, a drowsiness value may advantageously be used which was determined in a prior time interval. By this is to be understood that the prior time interval lies prior in time to the time interval to be assessed. Advantageously, the time interval to be assessed directly follows the prior time interval. Thus, to estimate the present sleepiness of the driver, use is therefore made not only of the ascertained input data valid for this point in time, but rather, the sleepiness or drowsiness estimated in a previous step is also used as input feature within the context of a feedback loop.

The drowsiness value of the previous period of time represents a suitable indicator for the present drowsiness, since it does not change abruptly to a great extent. By considering an ascertained drowsiness value of a prior time interval, advantageously a reference may be facilitated to the previous period of time when determining the current drowsiness value. Consequently, the quality of the result is advantageously increased by the fact, for example, that the influence of time-limited events or incorrect measurements may be reduced.

In one embodiment, the method is characterized by the following steps:
  Determining the drowsiness value for the prior time interval, while taking account of data ascertained with respect to the drowsiness characteristic over the prior time interval,
  Storing the drowsiness value of the prior time interval,
  Determining the drowsiness value for the time interval to be assessed, while taking into account data ascertained with respect to the drowsiness characteristic over the time interval to be assessed, as well as in due consideration of the drowsiness value stored for the prior time interval.

Furthermore, the following steps may precede the method or be integrated into the method: Definition and establishment of the drowsiness characteristic (or characteristics), ascertainment of the data with regard to the drowsiness characteristic, preprocessing of data ascertained with regard to the drowsiness characteristic.

By this is understood that the drowsiness values are stored over the medium term for later weighting and ascertainment of a drowsiness characteristic of a subsequent time interval. By such an approach, drowsiness characteristics already determined may advantageously be taken into account using a simple arrangement, in the sense of a feedback loop.

In one embodiment, the method is characterized in that ascertained drowsiness values of several prior time intervals are taken into account as drowsiness base value, in particular, the prior time intervals being consecutive time intervals.

This may be understood to mean that the drowsiness base value may be formed not only by the use of one earlier determined drowsiness value—as already explained—but also may take into account and include a multitude of earlier determined drowsiness values. In addition, it is understood that the prior time intervals lie chronologically before the time interval to be assessed. Furthermore, the prior time intervals advantageously represent consecutive time intervals. Additionally, the time interval to be assessed directly follows one of the prior time intervals chronologically.

In this manner, a multitude of already ascertained drowsiness values of prior time intervals may advantageously be taken into account. The quality of the results may thereby be increased. In addition, further factors may advantageously be derived from them, for example, information about the history and the progression of the drowsiness values. Extrapolations may also be derived, for example.

Furthermore, for example, the occurrence of extreme values with regard to the ascertained drowsiness values of earlier time intervals are able to be recognized. As a rule, sleepiness develops continuously. By taking several earlier values into account, a development may be estimated and, if applicable, extreme values may also be averaged. Such outliers may have both driver-specific reasons and metrological reasons. With knowledge thereof, such an existing situation may be taken into account, for example, in the form of the smoothing of results, by giving less regard to ascertained extreme values ("outliers").

In an alternative further refinement, the method is characterized by the following steps:
  Determining the drowsiness values for the prior time intervals, while taking account of data ascertained with respect to the drowsiness characteristic over the respective prior time interval,
  Storing the drowsiness values of the prior time intervals,
  Determining the drowsiness value for the time interval to be assessed, while taking into account data ascertained with respect to the drowsiness characteristic over the time interval to be assessed, as well as in due consideration of the drowsiness values stored for the prior time intervals.

In one advantageous embodiment, the method is characterized in that in determining the drowsiness value for the time interval to be assessed, the ascertained drowsiness values of the prior time intervals are weighted.

This is understood to mean that the ascertained drowsiness values of earlier time intervals may also be taken into consideration to varying degree. For example, it is thereby advantageously possible to give less weight to values from longer ago than to values that are more recent. Naturally, values as of a certain distance in the past may also be completely disregarded. This has influence on the calculation of the drowsiness value for the time interval to be assessed. Consequently, the quality of the result may advantageously be improved.

In one embodiment, the method is characterized in that in determining the drowsiness value for the time interval to be assessed, a characteristic curve of the ascertained drowsiness values of the prior time intervals is taken into consideration.

By this is understood that when determining the instantaneous drowsiness value, a development of the ascertained drowsiness values over time may be considered. In particular, a characteristic curve is understood to be a time sequence. In this case, for example, the magnitude of change and the rate of change of the ascertained drowsiness values over time may be analyzed and taken into account. Such a history as well as developments over time may be used advantageously as suitable indicator for future developments. For example, an extrapolation is possible on such a basis. Such an extrapolation—for instance, in addition to the drowsiness characteristics actually determined for the time interval to be assessed—may be utilized in determining the instantaneous drowsiness value.

In one embodiment, the method is characterized in that in determining the drowsiness value for the time interval to be assessed, a defined initial value is taken into account as drowsiness base value, particularly for the case of a driver change and/or for the case when no drowsiness value from a prior time interval is available.

This means that an initial drowsiness value is defined and utilized if no drowsiness value ascertained for the driver is available from a prior time interval. For example, this is possible at the commencement of travel or upon start of the assistance system. Pauses during travel may also represent an interruption of the kind which requires re-determination of the drowsiness value, and values determined up to that point should not be built upon. In this context, the initial value may be preset as a fixedly defined value, or may also be estimated as a function of further factors for the specific situation and/or driver. By using an initial drowsiness value as drowsiness base value, it is possible to avoid a snapshot in time for the first measuring interval or first measuring intervals. Advantageously, the quality of the results may thereby be optimized, especially with regard to accuracy and assurance of the information quality.

In one advantageous further refinement, the method is characterized in that the initial value is defined as a function of the time of day.

This is understood to mean that the magnitude or amount of the initial drowsiness value used is set as a function of situative parameters. In particular, the time of day seems suitable to reflect the circadian rhythm of the driver and to permit an appropriate presetting of the system. Alternatively, clock time, brightness or similar parameters which are able to appropriately reflect the circadian rhythm are also conceivable.

In one embodiment, the method is characterized in that one or more drowsiness characteristics is/are ascertained and/or evaluated in order to determine the drowsiness value for the time interval to be assessed and/or the drowsiness value of a prior time interval.

As already explained, a drowsiness value is determined on the basis of a drowsiness characteristic. In this connection, advantageously, the use of several different drowsiness characteristics may also be provided. This means that all defined drowsiness characteristics are evaluated over the respective time interval in order to determine the drowsiness value. By taking several parameters, that is, several different drowsiness characteristics into consideration, the quality of the result may be further increased.

In an alternative embodiment, the method is characterized in that data, especially ascertained data, is preprocessed to determine the drowsiness value.

The data is ascertained depending on the specific drowsiness characteristic. For instance, an infrared camera may be employed to determine eyelid closures. Naturally, the data thereby ascertained and subsequently to be processed relates to the specific drowsiness characteristic. Numerous methods, processes and arrangement are believed to be understood for preprocessing this data, such as averaging the parameters of the time interval. By this process step, the ascertained data may advantageously be brought to a state which makes it possible to determine the drowsiness value.

In one advantageous further refinement, the method is characterized in that data, especially ascertained and/or stored and/or defined data, is processed in order to determine the drowsiness value.

In particular, defined initial values (as drowsiness value) are to be understood as defined data. Drowsiness values already determined from prior time intervals are especially to be understood as ascertained and/or stored data. Alternatively, drowsiness characteristics from prior time intervals, i.e., the values of the drowsiness characteristics over the time steps of the respective time interval, may also be used in this connection. Various methods, processes and arrangements are available for processing the data as well as for determining the drowsiness values. The following may be named by way of example: multiple linear regression, decision trees, artificial neural networks.

In one configuration, the method is characterized in that, on the basis of the drowsiness value for the time interval to be assessed, a further action following the determination of the drowsiness value for the time interval to be assessed is defined.

This is understood to mean that the magnitude of the ascertained drowsiness value may trigger further method steps. For example, if the ascertained drowsiness value points to critical drowsiness on the part of the driver, a corresponding signal may advantageously be output in order to activate information. For instance, such information may represent an indication or an explicit warning to the driver. By way of example, such a warning may be implemented acoustically and/or visually and/or haptically.

Furthermore, according to the present invention, an apparatus is provided which is furnished and configured to carry out the method described.

For this, advantageously a control device and/or another processing unit is provided for the motor vehicle, which is configured, that is, is set up and/or has an arrangement to carry out or to support a method as described above.

In addition, a driver assistance system is provided advantageously for a motor vehicle. The driver assistance system is characterized in that it is configured, that is, has an arrangement and is set up to carry out the method described when used as intended. Advantageously, the vehicle is provided with a passenger-compartment camera for photographing a driver. In addition, the vehicle is configured advantageously with a display for displaying information to the driver. The driver assistance system is configured advantageously to facilitate transmission of information to the driver, e.g., visually by a displayed coffee cup, or acoustically by warning signals or haptically by steering-wheel vibrations. Furthermore, the driver assistance system is advantageously configured to improve the attention of the driver, e.g., by intervening in the comfort functions of the vehicle such as adjusting the light in the passenger compartment, activation or variation of music, control of the passenger-compartment temperature, etc.

Also of advantage is a computer-program product or computer program having program code that may be stored on a machine-readable carrier or storage medium such as a semiconductor memory, a hard-disk storage or an optical memory, and is used to carry out, implement and/or control the steps of the method according to one of the previously described specific embodiments, especially when the program product or program is executed on a computer or a device.

It should be pointed out that the features specified in the description may be combined with each other in any technically useful manner, and demonstrate further embodiments of the invention. Additional features and functionality of the present invention are derived from the description of exemplary embodiments with reference to the accompanying figures.

DETAILED DESCRIPTION

Figure 1:
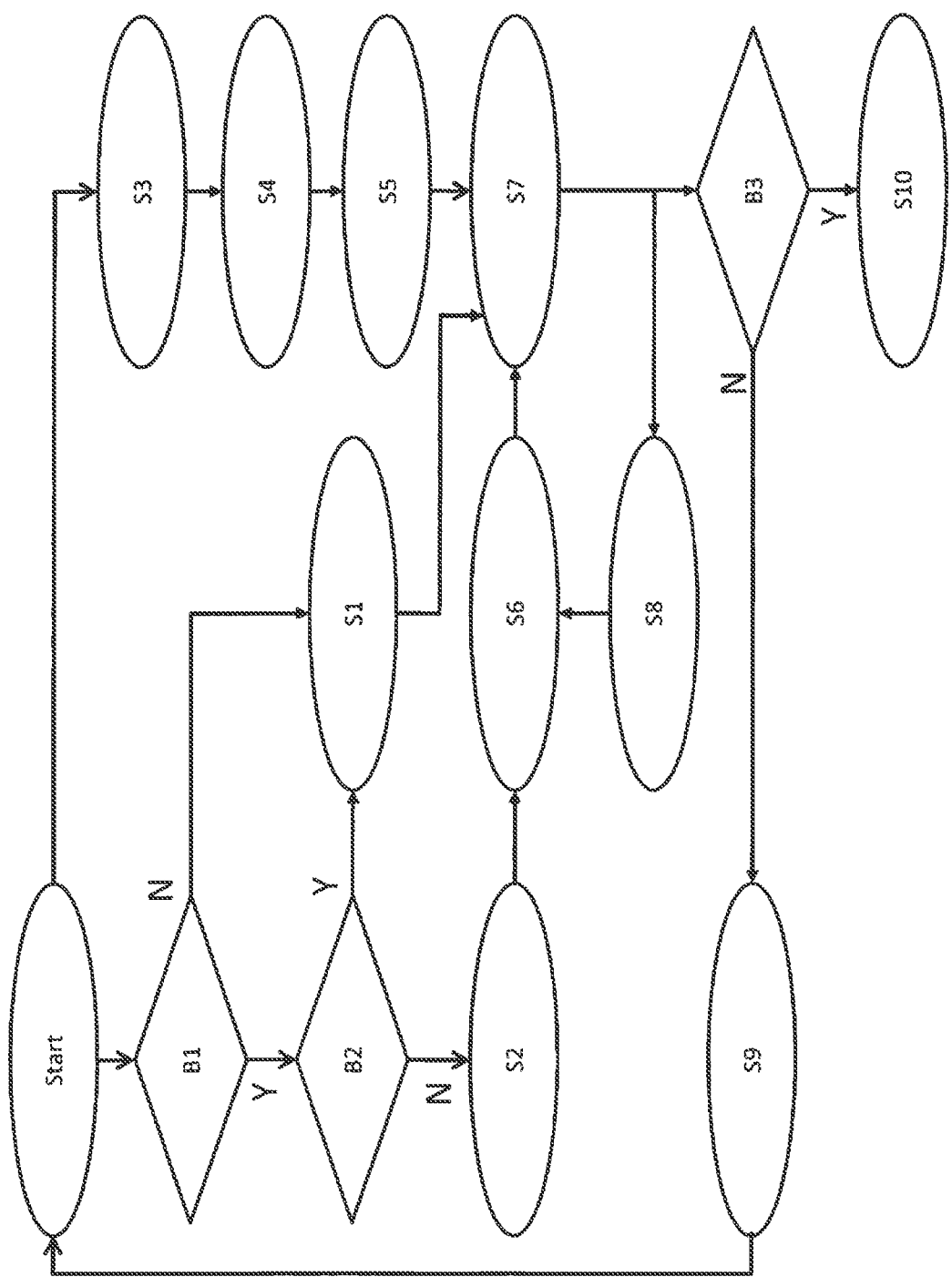
FIG. 1 shows a process diagram of the method according to one possible embodiment.

FIG. 1 shows a representation of an exemplary method. The method is made up of various steps S, which in part are dependent on decisions or conditions B. After the start of the method, initially a first check B1 is made as to whether a drowsiness value determined from a prior time interval is already available. If this condition is satisfied—represented by the letter Y—in a second condition B2, it is checked whether a change of driver has taken place.

If condition B1 is not satisfied—represented by the letter N—, that is, no drowsiness value is available from a prior time interval, in a step S1, a defined initial value is selected for the subsequent determination of a drowsiness value. This initial value may be defined as a function of the time of day. Personal characteristics of the specific driver may also be taken into account.

Likewise, a defined initial value is selected for the subsequent determination if the second condition B2 is satisfied, that is, if a driver change has been identified.

If the second condition B2 is not satisfied, that is, if no driver change has been identified, the drowsiness value determined from the prior time interval is taken into account. The determination on this takes place in step S2. Should several drowsiness values from several prior time intervals already be available, they may also be taken into account accordingly. For this, the corresponding values are suitably weighted in a further step S6. This weighting may take into account the time characteristic of the determination. Step S6 is therefore to be understood as optional.

Furthermore, subsequent to the start of the method, in a step S3, data is collected concerning one or more defined drowsiness characteristics. In a step S4, preprocessing is carried out with regard to the data thus ascertained. In this connection, it is pointed out that steps S3 and S4 are to be understood as optional. Naturally, externally ascertained raw data as well as preprocessed data may also be integrated into the process. In addition, a parameter calculation is carried out in a step S5. In so doing, for example, eyelid blinking events are calculated.

In a subsequent step S7, the drowsiness value of the time interval to be assessed is determined. In doing so, the drowsiness is classified. For this determination, both information and data with respect to the drowsiness characteristic(s) of the time interval to be assessed are considered, as well as a further drowsiness base value. For instance, a defined initial value or an ascertained drowsiness value of a prior, that is, earlier time interval may be used for this purpose. Of course, several drowsiness values determined from several prior time intervals may also be used. In addition, they may undergo a weighting process in step S6.

In order for the determined drowsiness value of the time interval to be assessed to be taken into account for subsequent time intervals, the value is stored in step S8 shown. In this way, the ascertained drowsiness value, for example, in the next time interval, may be included in the weighting in step S6.

Following the determination of the drowsiness value and classification of the drowsiness in step S7, in condition B3, it is checked whether the ascertained drowsiness of the driver lies in a critical range. If this is the case (case Y), a suitable defined action is carried out. Thus, for example, the driver may be warned. For this, the method may generate a signal, for instance, and transmit it to the suitable device. If the ascertained drowsiness does not lie in the critical range (case N), the method is carried out for the next following time interval.

Figure 2:
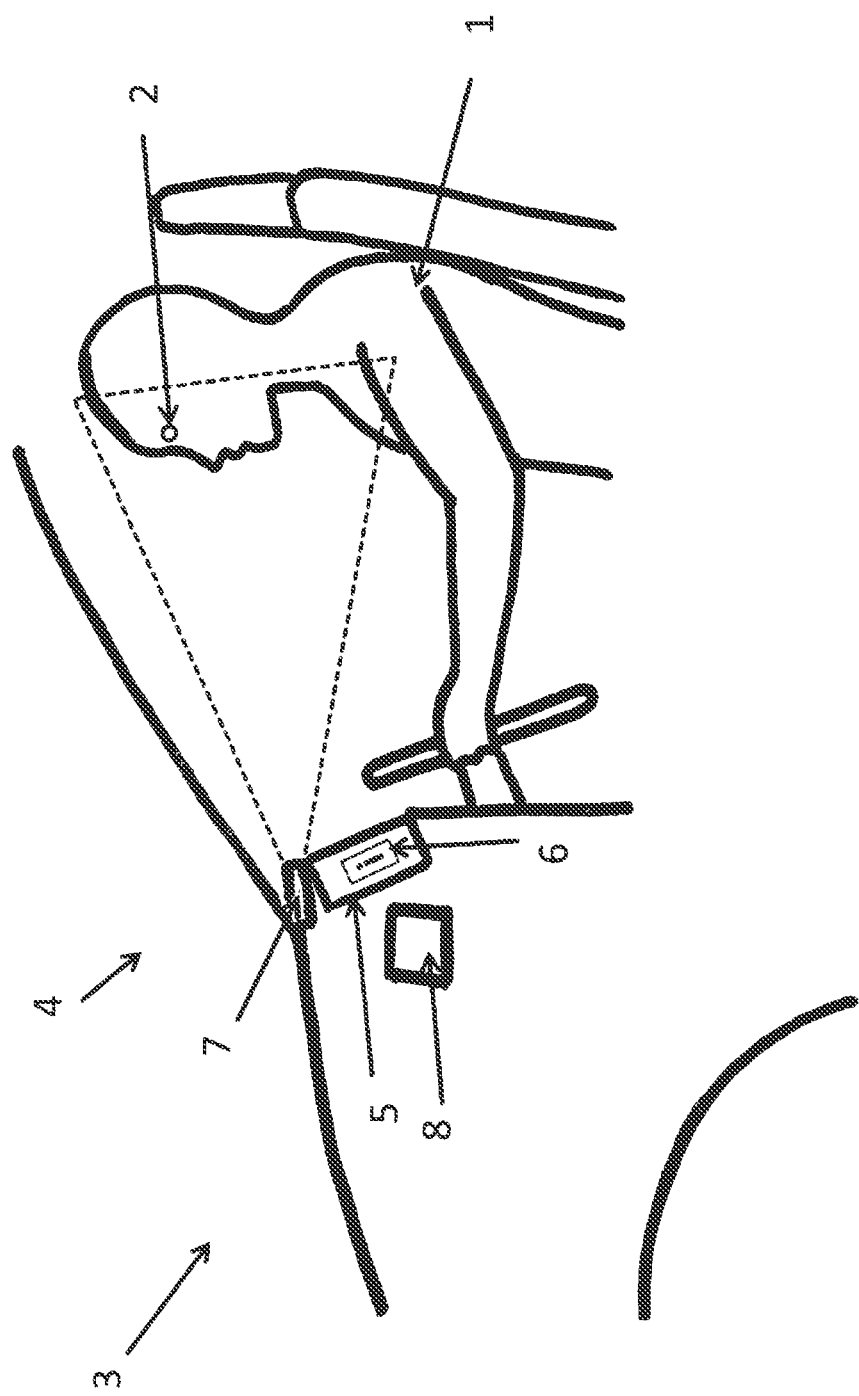
FIG. 2 shows a schematic representation of the devices for the practical application of the method in a motor vehicle according to one possible embodiment.

FIG. 2 shows a schematic representation of an exemplary apparatus for the practical application of the method in a motor vehicle. Here, a driver 1 is shown in a motor vehicle 3. Vehicle 3 has a driver assistance system 4 for determining the drowsiness of driver 1. To that end, drowsiness characteristics are monitored with the aid of a passenger-compartment sensor system 7. In the embodiment shown, the closing behavior of eyes 2 of driver 1 is monitored by passenger-compartment sensor system 7 in the form of a camera. Furthermore, a regulating and control device 8 is provided to carry out the method. In addition, this regulating and control device 8 may also be set up to preprocess the data ascertained with the aid of passenger-compartment sensor system 7 and/or to carry out a parameter calculation. Moreover, a device 5 is provided for the output of information 6 to driver 1. This device 5 takes the form of a display which outputs visual warning signs as information 6 to the driver. Naturally, devices are also [possible] (e.g., loudspeaker), which permit an auditory transmission (for example, via loudspeaker) or haptic transmission (e.g., with the aid of steering-wheel or seat vibrations) of information 6 to driver 1.

What is claimed is:

1. A method for determining a drowsiness value that represents the drowsiness of a driver of a motor vehicle, the method comprising:
   determining the drowsiness value cyclically over defined time intervals on the basis of at least one drowsiness characteristic;
   wherein in determining a drowsiness value of a time interval to be assessed, in addition to the drowsiness characteristic, at least one drowsiness base value is taken into account;
   wherein in determining the drowsiness value for the time interval to be assessed, ascertained drowsiness values of prior consecutive time intervals are weighted and used for the determination, the ascertained drowsiness values of the prior intervals occurring earlier in time being given less weight than ascertained drowsiness values of the prior intervals occurring later in time;

transmitting a signal to trigger a warning to the driver based on the drowsiness value, the warning being at least one of a visual warning, an auditory warning, and a haptic warning.

2. The method of claim 1, wherein an ascertained drowsiness value of a prior time interval is taken into account as drowsiness base value.

3. The method of claim 2, further comprising:
determining the drowsiness value for the prior time interval, while taking account of data ascertained with respect to the drowsiness characteristic over the prior time interval;
storing the drowsiness value of the prior time interval; and
determining the drowsiness value for the time interval to be assessed, while taking into account data ascertained with respect to the drowsiness characteristic over the time interval to be assessed, as well as in due consideration of the drowsiness value stored for the prior time interval.

4. The method of claim 1, wherein in determining the drowsiness value for the time interval to be assessed, a characteristic curve of the ascertained drowsiness values of the prior time intervals is taken into account.

5. The method of claim 1, wherein the initial value is defined as a function of the time of day.

6. The method of claim 1, wherein one or more drowsiness characteristics is/are ascertained and/or evaluated in order to determine the drowsiness value for the time interval to be assessed and/or the drowsiness value of a prior time interval.

7. The method of claim 1, wherein data, especially ascertained data, is preprocessed to determine the drowsiness value.

8. The method of claim 1,
wherein data, especially ascertained and/or stored and/or defined data, is processed in order to determine the drowsiness value.

9. An apparatus for determining a drowsiness value that represents the drowsiness of a driver of a motor vehicle, comprising:
a control device to determine the drowsiness value cyclically over defined time intervals on the basis of at least one drowsiness characteristic;
wherein in determining a drowsiness value of a time interval to be assessed, in addition to the drowsiness characteristic, at least one drowsiness base value is taken into account;
wherein in determining the drowsiness value for the time interval to be assessed, ascertained drowsiness values of prior consecutive time intervals are weighted and used for the determination, the ascertained drowsiness values of the prior intervals occurring earlier in time being given less weight than ascertained drowsiness values of the prior intervals occurring later in time; and
wherein the control device transmits a signal to trigger a warning to the driver based on the drowsiness value, the warning being at least one of a visual warning, an auditory warning, and a haptic warning.

10. A non-transitory computer readable medium having a computer program, which is executable by a computer, comprising:
a program code arrangement having program code for determining a drowsiness value that represents the drowsiness of a driver of a motor vehicle, by performing the following:
determining the drowsiness value cyclically over defined time intervals on the basis of at least one drowsiness characteristic;
wherein in determining a drowsiness value of a time interval to be assessed, in addition to the drowsiness characteristic, at least one drowsiness base value is taken into account;
wherein in determining the drowsiness value for the time interval to be assessed, ascertained drowsiness values of prior consecutive time intervals are weighted and used for the determination, the ascertained drowsiness values of the prior intervals occurring earlier in time being given less weight than ascertained drowsiness values of the prior intervals occurring later in time; and
transmitting a signal to trigger a warning to the driver based on the drowsiness value, the warning being at least one of a visual warning, an auditory warning, and a haptic warning.

11. The non-transitory computer readable medium of claim 10, wherein an ascertained drowsiness value of a prior time interval is taken into account as drowsiness base value.

12. The method of claim 1, further comprising:
monitoring a closing behavior of eyes of the driver using a camera; and
determining the drowsiness characteristic based on the monitoring.

13. The method of claim 1, further comprising:
displaying the visual warning on a display device.

14. The method of claim 1, further comprising:
outputting the auditory warning using a speaker.

15. The method of claim 1, further comprising:
vibrating at least one of a steering-wheel and a seat as the haptic warning.

16. The method of claim 1, wherein the determining and the triggering steps are performed via a control device.

* * * * *